(12) United States Patent
Sridharan

(10) Patent No.: US 9,095,547 B2
(45) Date of Patent: Aug. 4, 2015

(54) STRUCTURE ASSESSMENT OF HETEROGENEOUS POLYPEPTIDE MIXTURE

(71) Applicant: Momenta Pharmaceuticals, Inc., Cambridge, MA (US)

(72) Inventor: Ramamurthi Sridharan, Acton, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/651,119

(22) Filed: Oct. 12, 2012

(65) Prior Publication Data

US 2013/0041176 A1  Feb. 14, 2013

Related U.S. Application Data

(63) Continuation of application No. PCT/US2012/046246, filed on Jul. 11, 2012.

(60) Provisional application No. 61/506,398, filed on Jul. 11, 2011.

(51) Int. Cl.
*C07K 1/06* (2006.01)
*C07K 14/00* (2006.01)
*A61K 38/16* (2006.01)

(52) U.S. Cl.
CPC ............... *A61K 38/16* (2013.01); *C07K 1/061* (2013.01); *C07K 14/001* (2013.01); *Y10S 514/903* (2013.01)

(58) Field of Classification Search
CPC . G01N 21/19; G01N 2021/216; A61K 38/16; C07K 14/001
See application file for complete search history.

(56) References Cited

U.S. PATENT DOCUMENTS

| 3,849,550 A | 11/1974 | Teitelbaum et al. |
| 2006/0154862 A1 | 7/2006 | Ray et al. |
| 2007/0021324 A1 | 1/2007 | Dolitzky |
| 2007/0054857 A1 | 3/2007 | Pinchasi et al. |
| 2007/0059798 A1 | 3/2007 | Gad et al. |
| 2009/0263347 A1 | 10/2009 | Jiang et al. |
| 2010/0256039 A1 | 10/2010 | Coleman et al. |
| 2010/0331266 A1 | 12/2010 | Jiang et al. |
| 2011/0183426 A1* | 7/2011 | Chan et al. ............ 436/86 |
| 2014/0288269 A1* | 9/2014 | Venkata et al. ........ 530/344 |

FOREIGN PATENT DOCUMENTS

| WO | 95/31990 | 5/1995 |
| WO | 2006/029411 | 3/2006 |
| WO | 2010/017292 | 2/2010 |

OTHER PUBLICATIONS

Greenfield, N. et al. "Computed Circular Dichroism Spectra for Evaluation of Protein Conformation," Biochemistry 8, 1969, 4108-4116.*
Vila et al., "Physical reasons for the unusual α-helix stabilization afforded by charged or neutral polar residues in alanine-rich peptides," PNAS 97(24):13075-13079 (2000).
Teitelbaum et al., "Suppression of experimental allergic encephalomyelitis by a synthetic polypeptide", Eur. J. Immunol., 1:242-248, 1971.
Varkony et al., "The glatiramoid class of immunomodulator drugs", Expert Opin. Pharmacother., 10(4):657-668, 2009.

* cited by examiner

*Primary Examiner* — Yelena G Gakh
*Assistant Examiner* — Michelle Adams
(74) *Attorney, Agent, or Firm* — Fish & Richardson P.C.

(57) ABSTRACT

Glatiramer acetate containing compositions and drug products can be manufactured using methods that include a step of measuring one or both of the alpha helical content of the glatiramer acetate and the random coil content of the glatiramer acetate. These measurements can be compared to particular values or ranges for one or both of alpha helical and random coil content. The results of the comparison can be used in determining whether a given batch of glatiramer acetate should be used to manufacture a glatiramer acetate-containing drug product. The measurement of alpha helical content of the glatiramer acetate and the random coil content can be carried out using various methods, including circular dichroism.

9 Claims, No Drawings

STRUCTURE ASSESSMENT OF HETEROGENEOUS POLYPEPTIDE MIXTURE

This application is a continuation of and claims priority under 35 U.S.C 120 to PCT Application No. PCT/US2012/046246, filed Jul. 12, 2011, which claims priority to U.S. Provisional Application No. 61/506,398 filed on Jul. 11, 2011, the entire contents of which applications are incorporated herein by reference in their entirety.

TECHNICAL FIELD

The present disclosure relates to methods of assessing the structure of heterogeneous polypeptide mixtures, for example, glatiramer acetate (GA), and for making (e.g., manufacturing or producing) GA and/or polymeric precursors of GA.

BACKGROUND

Glatiramer acetate (GA), marketed commercially as COPAXONE®, consists of the acetate salts of synthetic polypeptides containing four naturally occurring amino acids: L-glutamic acid, L-alanine, L-tyrosine, and L-lysine, with a reported average molar fraction of 0.141, 0.427, 0.095, and 0.338, respectively. Chemically, GA is designated L-glutamic acid polymer with L-alanine, L-lysine and L-tyrosine, acetate (salt). Its structural formula is:

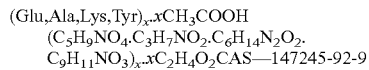

(Glu,Ala,Lys,Tyr)$_x$·$x$CH$_3$COOH
(C$_5$H$_9$NO$_4$·C$_3$H$_7$NO$_2$·C$_6$H$_{14}$N$_2$O$_2$·
C$_9$H$_{11}$NO$_3$)$_x$·$x$C$_2$H$_4$O$_2$ CAS—147245-92-9

Other than molecular weight and amino acid composition, which are specified in the approved label for the product, the label and other available literature for COPAXONE® does not provide detailed information about the physiochemical characteristics of the product.

SUMMARY

The present disclosure provides methods for assessing (e.g., measuring, analyzing, detecting, determining, evaluating, and/or estimating) the secondary structure of Glatiramer Acetate (GA) and, in some instances polymeric precursors of GA. The methods entail assessing the fraction of a sample of GA that is in alpha-helical conformation and/or assessing the fraction of a sample of GA that is in random coil conformation. The methods can be used, for example, for the selection of GA (e.g., upon completion of a manufacturing process) and/or polymeric precursors of GA (e.g., during a manufacturing process); to determine or confirm compliance of GA and/or polymeric precursors of GA with industrial and/or regulatory standards; to assess or confirm manufacturing consistency; as a quality control standard for use during manufacturing and/or against GA. Additional applications will be apparent to those of skill in the art based on the disclosure herein.

Described herein is a method of selecting a batch of a composition comprising glatiramer acetate, the method comprising: providing a batch of a composition comprising glatiramer acetate; measuring one or both of the alpha helical content of the glatiramer acetate and the random coil content of the glatiramer acetate in the batch; and selecting the batch if (e.g., if and only if): i) the alpha helical content of the glatiramer acetate in the batch is within a predetermined range for alpha helical content, 2) the random coil content of the glatiramer acetate in the batch is within a predetermined range for random coil content, or 3) the alpha helical content of the glatiramer acetate in the batch is within a predetermined range for alpha helical content and the random coil content of the glatiramer acetate in the batch is within a predetermined range for random coil content, thereby selecting a batch of a composition comprising glatiramer acetate.

Also described herein is a method of preparing a pharmaceutical composition comprising glatiramer acetate, the method comprising: providing a batch of a composition comprising glatiramer acetate; measuring one or both of the alpha helical content of the glatiramer acetate and the random coil content of the glatiramer acetate in the batch; selecting the batch for use in the preparation of a pharmaceutical composition if (e.g., if and only if): i) the alpha helical content of the glatiramer acetate in the batch is within a predetermined range for alpha helical content, 2) the random coil content of the glatiramer acetate in the batch is within a predetermined range for random coil content, or 3) the alpha helical content of the glatiramer acetate in the batch is within a predetermined range for alpha helical content and the random coil content of the glatiramer acetate in the batch is within a predetermined range for random coil content; and preparing a pharmaceutical composition comprising at least a portion of the selected batch.

In various cases: the predetermined range for alpha helical content is 48.1%-71.2% when the alpha-helical content of the glatiramer acetate is measured at 5° C. in 10 mM sodium phosphate at pH 7.0; the predetermined range for alpha helical content is 51.0%-68.1% when the alpha-helical content of the glatiramer acetate is measured at 5° C. in 10 mM sodium phosphate at pH 7.0; and the predetermined range for alpha helical content is 53.8%-65.0% when the alpha-helical content of the glatiramer acetate is measured at 5° C. in 10 mM sodium phosphate at pH 7.0; the step of measuring the alpha helical or random coil content comprises taking a circular dichroism spectra of a sample of the glatiramer acetate in the batch and interpreting the circular dichroism spectra; the step of interpreting the circular dichroism spectra comprises assuming (e.g., based on empirical data described herein) that all of the glatiramer acetate is either alpha helical conformation or random coil conformation; and the composition comprising glatiramer acetate is selected from the group consisting of: a drug substance (DS, (e.g., soluble and/or lyophilized (e.g., dry) GA DS)) and a drug product (DP).

Because the alpha-helical and or random coil content need not be measured as exemplified (e.g., using the conditions) herein, e.g., at 5° C. in 10 mM sodium phosphate at pH 7.0, it should be understood that the actually measured alpha-helical or random coil content in a sample need not be within the actual ranges specified herein. Rather, it is enough that the actually measured alpha-helical or random coil content in a sample be equivalent to the ranges specified herein, e.g., if the alpha-helical or random coil content had been measured as exemplified (e.g., using the conditions) herein. For example, if the alpha-helical and or random coil content of the sample, however measured and whatever the value under the measurement condition, were measured at 5° C. in 10 mM sodium phosphate at pH 7.0 (e.g., by CD using the alpha-helix and random coil reference spectra for poly-lysine described herein (see e.g., Table 2)) alpha-helical and/or random coil content is desirably within one of the ranges described herein. In using reference spectra, the values for alpha-helical and beta-sheet content at one or more (e.g., 2, 3, 4, 5, 6, 7, 8, 9, 10, 11, 12, 13 14, 15 or 16) of the wavelengths can be used.

In various cases: the measuring step comprises: providing a value for the alpha helical content and comparing the value to a reference value or range for alpha helical content, providing a value for the random coil content and comparing the value to a reference value or range for random coil content, or both providing a value for the alpha helical content and comparing the value to a reference value or range for alpha helical content and providing a value or range for the random coil content and comparing the value to a reference value or range for random coil content; the reference value or range for alpha helical content is a specification for commercial release of glatiramer acetate, the reference value or range for random coil content is a specification for commercial release of glatiramer acetate, or the reference value or range for alpha helical content; the reference value or range for random coil content are specifications for commercial release of glatiramer acetate; and the composition containing glatiramer acetate comprises mannitol.

In some cases the method includes additional steps, for example, if the value for alpha helical content has a preselected relationship with the reference value or range for alpha helical content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce.

In some cases the method includes additional steps, for example, if the value for random coil content has a preselected relationship with the reference value or range for random coil content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce.

In some cases the methods includes: measuring the alpha helical content of the glatiramer acetate or the random coil content of the glatiramer acetate or both the alpha helical content and random coil content of the glatiramer acetate in at least a first and a second sample of the batch; providing and evaluating at least two batches; designating the selected batch as suitable for sale or administration to a human; designating the pharmaceutical composition as suitable for sale or administration to a human.

Also described herein is a method for preparing a pharmaceutical composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and purifying the glatiramer acetate, wherein the improvement comprises: measuring one or both of the alpha helical content of the purified glatiramer acetate and the random coil content of the purified glatiramer acetate.

In some cases the method for preparation of the pharmaceutical composition includes: selecting the purified glatiramer acetate for use in the preparation of a pharmaceutical composition if: the alpha helical content of the purified glatiramer acetate is within a predetermined range for alpha helical content, 2) the random coil content of the purified glatiramer acetate is within a predetermined range for random coil content, or 3) the alpha helical content of the purified glatiramer acetate is within a predetermined range for alpha helical content and the random coil content of the purified glatiramer acetate is within a predetermined range for random coil content.

In some cases the method for preparation of the pharmaceutical composition includes: preparing a pharmaceutical composition comprising at least a portion of the selected purified glatiramer acetate.

In various embodiments of the preparation method: the predetermined range for alpha helical content is 48.1%-71.2% when the alpha-helical content of the glatiramer acetate is measured at 5° C. in 10 mM sodium phosphate at pH 7.0; the predetermined range for alpha helical content is 51.0%-68.1% when the alpha-helical content of the glatiramer acetate is measured at 5° C. in 10 mM sodium phosphate at pH 7.0; and the predetermined range for alpha helical content is 53.8%-65.0% when the alpha-helical content of the glatiramer acetate is measured at 5° C. in 10 mM sodium phosphate at pH 7.0; the step of measuring the alpha helical or random coil content comprises taking a circular dichroism spectra of a sample of the glatiramer acetate in the batch and interpreting the circular dichroism spectra; the step of interpreting the circular dichroism spectra comprises assuming that all of the glatiramer acetate is either alpha helical conformation or random coil conformation; the composition comprising glatiramer acetate is selected from the group consisting of: a drug substance (DS) or a drug product (DP); and the composition containing glatiramer acetate comprises mannitol.

Also described is a method of identifying a batch of a composition comprising a copolymer (e.g., copolymer of glutamic acid, alanine tyrosine and lysine; a copolymer of glutamic acid, alanine tyrosine and lysine with a reported average molar fraction of 0.141, 0.427, 0.095, and 0.338, respectively; or a copolymer of glutamic acid, alanine tyrosine and lysine with a reported average molar fraction of 0.141, 0.427, 0.095, and 0.338, respectively, and a peak average molecular weight of 5,000-7,000) as a batch of a composition comprising glatiramer acetate, the method comprising: providing a batch of a composition comprising a copolymer of tyrosine, lysine, alanine and glutamic acid; measuring one or both of the alpha helical content of the glatiramer acetate and the random coil content of the copolymer in the batch; and identifying the batch of the copolymer as glatiramer acetate if: i) the alpha helical content of the copolymer in the batch is within a predetermined range for alpha helical content of glatiramer acetate, 2) the random coil content of the copolymer in the batch is within a predetermined range for random coil content or glatiramer acetate, or 3) the alpha helical content of the copolymer in the batch is within a predetermined range for alpha helical content of glatiramer acetate and the random coil content of the coplymer in the batch is within a predetermined range for random coil content of glatiramer acetate, thereby identifying a batch of a composition comprising a copolymer of tyrosine, lysine, alanine and glutamic acid as a batch of a composition comprising glatiramer acetate.

Also described is a method of preparing a pharmaceutical composition comprising glatiramer acetate, the method comprising: providing a batch of a composition comprising a copolymer (e.g., copolymer of glutamic acid, alanine tyrosine and lysine; a copolymer of glutamic acid, alanine tyrosine and lysine with a reported average molar fraction of 0.141, 0.427, 0.095, and 0.338, respectively; or a copolymer of glutamic acid, alanine tyrosine and lysine with a reported average molar fraction of 0.141, 0.427, 0.095, and 0.338, respectively, and a peak average molecular weight of 5,000-7,000); measuring one or both of the alpha helical content of the copolymer and the random coil content of the copolymer in the batch; selecting the batch for use in the preparation of a pharmaceutical composition comprising glatiramer acetate if: i) the alpha helical content of the copolymer in the batch is within a predetermined range for alpha helical content of glatiramer acetate, 2) the random coil content of the copolymer in the batch is within a predetermined range for random coil content of glatiramer acetate, or 3) the alpha helical content of the copolymer in the batch is within a predetermined range for alpha helical content of glatiramer acetate and the random coil content of the copolymer in the batch is within a predetermined range for random coil content of glatiramer acetate; and preparing a pharmaceutical composition comprising glatiramer acetate from at least a portion of the selected batch.

In various cases of the identification method: the predetermined range for alpha helical content is 48.1%-71.2% when the alpha-helical content of the glatiramer acetate is measured at 5° C. in 10 mM sodium phosphate at pH 7.0; the predetermined range for alpha helical content is 51.0%-68.1% when the alpha-helical content of the glatiramer acetate is measured at 5° C. in 10 mM sodium phosphate at pH 7.0; the predetermined range for alpha helical content is 53.8%-65.0% when the alpha-helical content of the glatiramer acetate is measured at 5° C. in 10 mM sodium phosphate at pH 7.0; the step of measuring the alpha helical or random coil content comprises circular dichroism analysis of a sample of the batch of glatiramer acetate; the circular dichroism analysis comprises deconvultion of the spectra using a model that assumes that all of the glatiramer acetate is either alpha helical conformation or random coil conformation; the circular dichroism analysis comprises deconvultion of the spectra using the reference spectra in Table 2; the measuring step comprises: providing a value for the alpha helical content and comparing the value to a reference value or range for alpha helical content, providing a value for the random coil content and comparing the value to a reference value or range for random coil content, or both providing a value for the alpha helical content and comparing the value to a reference value or range for alpha helical content and providing a value or range for the random coil content and comparing the value to a reference value or range for random coil content; the reference value or range for alpha helical content is a specification for commercial release of glatiramer acetate, the reference value or range for random coil content is a specification for commercial release of glatiramer acetate, or the reference value or range for alpha helical content and the reference value or range for random coil content are specifications for commercial release of glatirmer acetate.

In some cases the identification methods includes one or more additional steps, for example: if the value for alpha helical content has a preselected relationship with the reference value or range for alpha helical content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce.

In some cases the identification method includes: if the value for random coil content has a preselected relationship with the reference value or range for random coil content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce; measuring the alpha helical content of the glatiramer acetate or the random coil content of the glatiramer acetate or both the alpha helical content and random coil content of the glatiramer acetate in at least a first and a second sample of the batch; providing and evaluating at least two batches; designating the selected batch as suitable for sale or administration to a human; designating the pharmaceutical composition as suitable for sale or administration to a human.

In various cases the method of preparing a pharmaceutical composition: the predetermined range for alpha helical content is 48.1%-71.2% when the alpha-helical content of the glatiramer acetate is measured at 5° C. in 10 mM sodium phosphate at pH 7.0; the predetermined range for alpha helical content is 51.0%-68.1% when the alpha-helical content of the glatiramer acetate is measured at 5° C. in 10 mM sodium phosphate at pH 7.0; the predetermined range for alpha helical content is 53.8%-65.0% when the alpha-helical content of the glatiramer acetate is measured at 5° C. in 10 mM sodium phosphate at pH 7.0; the step of measuring the alpha helical or random coil content comprises circular dichroism analysis of a sample of the batch of glatiramer acetate; the circular dichroism analysis comprises deconvultion of the spectra using a model that assumes that all of the glatiramer acetate is either alpha helical conformation or random coil conformation; the circular dichroism analysis comprises deconvultion of the spectra using the reference spectra in Table 2; the measuring step comprises: providing a value for the alpha helical content and comparing the value to a reference value or range for alpha helical content, providing a value for the random coil content and comparing the value to a reference value or range for random coil content, or both providing a value for the alpha helical content and comparing the value to a reference value or range for alpha helical content and providing a value or range for the random coil content and comparing the value to a reference value or range for random coil content; the reference value or range for alpha helical content is a specification for commercial release of glatiramer acetate, the reference value or range for random coil content is a specification for commercial release of glatiramer acetate, or the reference value or range for alpha helical content and the reference value or range for random coil content are specifications for commercial release of glatirmer acetate.

In some cases the method for preparing a pharmaceutical composition includes one or more additional steps, for example: if the value for alpha helical content has a preselected relationship with the reference value or range for alpha helical content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce.

In some cases the method for preparing a pharmaceutical composition includes: if the value for random coil content has a preselected relationship with the reference value or range for random coil content: classifying, selecting, accepting, discarding, releasing, or withholding a batch of glatiramer acetate; reprocessing a batch of glatiramer acetate through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce; measuring the alpha helical content of the glatiramer acetate or the random coil content of the glatiramer acetate or both the alpha helical content and random coil content of the glatiramer acetate in at least a first and a second sample of the batch; providing and evaluating at least two batches; designating the selected batch as suitable for sale or administration to a human; designating the pharmaceutical composition as suitable for sale or administration to a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and from the claims.

DETAILED DESCRIPTION

A process for the manufacture of Glatiramer Acetate (GA) generally includes the following steps:

Polymerization of N-carboxy anhydrides of L-alanine, benzyl-protected L-glutamic acid, trifluoroacetic acid (TFA) protected L-lysine and L-tyrosine (collectively referred to as NCAs) to result in a protected copolymer (Intermediate-1);

depolymerization and benzyl deprotection of Intermediate-1 using hydrobromic acid in acetic acid (e.g., phenol treated 33% HBr/acetic acid) to generate Intermediate-2; and deprotection of the TFA-protected lysines on Intermediate-2 (e.g., by treatment with piperdine) to create Intermediate-3, followed by processing to generate GA and further purification and drying of the isolated GA drug substance.

During polymerization, the NCAs are co-polymerized in a predetermined ratio using diethylamine as an initiator. Upon consumption of the NCA components, the reaction mixture is quenched in water. The resulting protected polymer (Intermediate-1) is isolated and dried. During depolymerization and benzyl deprotection, Intermediate-1 is treated with phenol-treated 33% HBr in acetic acid (HBr/AcOH) and water (see, e.g., U.S. Pat. No. 8,058,235). This step results in the cleavage of the benzyl protecting group on the glutamic acids as well as cleavage of peptide bonds throughout the polymer. After a period of time the reaction is quenched with water, and the product polymer is isolated by filtration and washed with water. The product polymer, Intermediate-2, has a reduced molecular weight relative to Intermediate-1. Intermediate-2 is dried before proceeding to deprotection of TFA-protected lysine. During deprotection of TFA-protected lysines, Intermediate-2 is treated with aqueous piperidine to remove the trifluoroacetyl group on the lysine. The resulting copolymer, Intermediate-3, is subsequently purified using diafiltration/ultrafiltration and the resulting acetate salt is dried to produce Glatiramer Acetate drug substance. Exemplary methods for the manufacture of GA are known in the art (see, for example, U.S. Pat. No. 3,849,550; WO 95/031990, US 2006/0154862, US 2007/0021324, US 2010/0256039, US 2007/0021324, US 2009/0263347, and US 2010/0256039, and WO 2010/017292 which are hereby incorporated by reference in their entirety).

The inventors have found that despite the heterogeneity of the polypeptide chains in GA there are certain detectable attributes of GA secondary structure that are conserved from batch-to-batch. As disclosed herein, these attributes can be assessed and such assessment can be used, e.g., to select GA or polymeric precursors of GA and/or to monitor, assess, and/or evaluate GA process and/or batch quality.

Secondary Structural Characteristics of GA

Based on detailed characterization of GA and the GA production process, the present disclosure provides that the secondary structure of GA, e.g., the secondary structure of GA as assessed by circular dichroism (CD) spectroscopy, is a conserved detectable attribute, a characteristic, hallmark, and/or a signature (e.g., a structural signature) of GA and/or the GA production process (e.g., polymeric precursors of GA). Accordingly, methods are described herein for assessing or evaluating the secondary structure of copolymers such as GA. The present disclosure further provides use of such assessment or evaluation to evaluate GA and/or whether a copolymer is (e.g., qualifies as) GA.

The secondary structure of a protein or a polypeptide in solution is dependent not only on its amino acid sequence but also on the solution conditions (e.g., pH, temperature, and ionic strength).

CD spectroscopy is commonly used to assess the secondary structure of proteins and polypeptides in solution. Proper analysis of the CD spectra of a protein or polypeptide in solution provides an empirical measurement of the portion of the protein or polypeptide that is alpha helical, beta sheet or random coil conformation under a given set of solution conditions.

CD spectroscopy is a desirable method for analyzing the secondary structure of a protein or a polypeptide in by virtue of its relative simplicity and speed. The amide chromophore of the polypeptide backbone absorbs strongly in the far ultraviolet region (190-240 nm). Local asymmetry, induced and modified by secondary structural variations of the polypeptide backbone, further modulates this absorbance, leading to CD spectra with characteristic fingerprints. Resolution of the secondary structure into its various components such as alpha-helix, beta-sheet, and random coil, is then accomplished by analyzing these spectra with suitable deconvolution algorithms.

CD spectroscopy is an empirical method and the results depend on the model assumed and on the reference spectra that is used as basis set for deconvolution. As such, it cannot provide an absolute quantification of the exact secondary structures. However, through the choice of a proper model that closely represents the system being analyzed and the proper choice of reference spectra, it is possible obtain a good estimate of the secondary structures.

GA is a mixture of polypeptides and is thus unlike the monodisperse polypeptides that are the usual subject of analysis by CD spectroscopy. In this context GA can be viewed as polydisperse and the assessed secondary structural quantity, e.g., the percent beta sheet, percent random coil and percent alpha helix, is a statistical average over all of the many different polypeptides present in GA. Accordingly, one might reasonably assume that any secondary structure quantification obtained by CD analysis would not be sufficiently sensitive, reproducible, and/or precise to be useful in assessing and/or selecting batches or lots of GA. Contrary to such reasonable assumptions, the inventor has found, surprisingly, as described herein, that the secondary structural composition of GA, which likely represents an average behavior of the polypeptides present, is in fact a reproducible characteristic of GA under well-defined solution conditions. These characteristics can readily be reproducibly and precisely measured and assessed by CD spectroscopy (e.g., in the range 190 nm-250 nm), providing a useful tool for assessment of GA, e.g., equivalence testing and/or identity testing.

The usefulness of the present CD secondary structure analysis is illustrated by an example below which shows that varying the process for producing GA by altering the timing of NCA addition or the length of the polymerization step can result in material that varies in alpha-helical from 11% to 65%, showing that changes in the GA manufacturing process can alter the secondary structure of the material produced. The usefulness of the present secondary structure analysis is also illustrated by an example below which shows that size fractionation of GA yields fractions that vary considerably in alpha-helical content.

There are several methods to extract the secondary structural information from the CD spectra, including multi-linear regression, singular value decomposition, ridge regression and neural network analysis. As described in greater detail below, linear regression analysis based on a two state model (random coil and alpha helical only) for GA yields useful results.

Methods are described herein for assessing (e.g., measuring, analyzing, detecting, determining, evaluating, estimating, and/or predicting) the secondary structure of GA or a polymeric precursor thereof by CD spectroscopy, although other suitable methods could be used. The methods include use of information from such assessment to determine the fraction of a sample of GA that is alpha-helical and/or the fraction that is random coil and optionally comparing the fraction to a reference standard for GA and/or a polymeric precursor of GA (e.g., a reference standard providing the fraction of alpha helical structure and random coil structure). Because the secondary structure of GA is a characteristic, hallmark, and/or signature (e.g., a structural signature) of GA and/or the GA production process, information pertaining to the secondary structure can be used to select, monitor, assess, and/or evaluate a GA process and/or batch quality.

The secondary structure of a sample GA or a precursor thereof can be assessed by determining the portion of the sample that is alpha helical and/or the portion that is random coil. The portion that is beta sheet need not be determined because the inventor has found that the portion of GA that is beta sheet is negligible, if present at all (e.g., when analyzed measured by CD spectroscopy in 10 mM sodium phosphate (pH 7.0).

Suitable ranges for the proportion of alpha helical and random coil in GA are shown in Table 1. Any of these ranges can be used a reference value (reference range) or a value (range) for comparison to a sample.

TABLE 1

|  | Alpha-helical portion (%) | Random coil portion (%) |
|---|---|---|
| Range A | 48.1 to 71.2 | 51.9 to 28.8 |
| Range B | 51.0 to 68.1 | 49.0 to 32.9 |
| Range C | 53.8 to 65.0 | 46.2 to 35.0 |

In some embodiments, a sample of GA or a polymeric precursor of GA can be selected if the portion of alpha helical conformation and/or random coil conformation of the GA has a preselected relationship with, is equal (e.g., about equal) to, is equivalent (e.g., about equivalent) to, and/or is consistent (i.e., within) with a range shown in Table 1.

In some embodiments, the portion of alpha helical structure or random coil structure is within a range shown in Table 1 when the measured by CD spectroscopy in 10 mM sodium phosphate (pH 7.0) at 5° C. (e.g., at 0.2 mg/ml). In some embodiments, the portion of alpha helical conformation and/or random coil conformation is within a range shown in Table 1 when measured by CD spectroscopy in 10 mM sodium phosphate (pH 7.0) at 5° C. and the spectra is deconvoluted using as the following reference spectra: a spectra for poly-lysine in alpha-helical form and a spectra for poly-lysine in random coil form (e.g., those described in: "Computed Circular Dichroism Spectra for the Evaluation of Protein Conformation" (Greenfield and Fasman, *Biochemistry,* 8:4108-4116, 1969)).

The methods discussed herein can be used to identify differences in GA materials that might not be observed using conventional methods (e.g., by analysis of molar mass and/or amino acid composition). By evaluating the secondary structure of GA or a polymeric precursor of GA, one can identify non-conforming compositions during or following the GA manufacturing process. Alternatively or in addition, the methods can be used to confirm consistency between initiation kinetics in GA production processes (e.g., to determine equivalence or compare consistency in initiation kinetics between lots of material). Comparisons can be made between two or more batches or lots of GA manufactured by different manufacturers, two or more batches or lots of GA manufactured at different locations, two or more batches or lots of GA manufactured at different times, two or more batches or lots of GA manufactured different processes, and/or two or more batches or lots of GA manufactured using altered or modified initiation kinetics. The methods described herein can also be used in quality control, e.g., to compare and/or confirm batch-to-batch consistency between lots made by a consistent process. The method described herein can be used to assess the equivalence of two samples of GA. The assessment can optionally include other measures such as amino acid content and molecular weight. The method described herein can be used to assess the identity of two samples of GA. The assessment can optionally include other measures such as amino acid content and molecular weight.

As used herein, GA includes, compositions comprising GA, a batch or batches, a sample or samples, and/or a lot or lots of GA. A batch of GA can be all or part of the product of a GA manufacturing process (e.g., all or part of a single manufacturing process or run). In some cases, one batch is analyzed. In some cases, two or more batches are analyzed. In other cases, multiple samples taken from a single batch are analyzed. A composition containing GA can be a drug substance (DS) (also known as an active pharmaceutical ingredient (API) or a drug product (DP). GA can also include GA before or after formulation as a drug product.

Selection of GA and/or polymeric precursors of GA can include selecting (e.g., for use or further processing) a sample of GA or a polymeric precursor of GA based on the secondary structure of the GA in the sample (e.g., based on comparison of portion of alpha helical and/or random coil structure in the sample with at least one reference value). For example, the methods can be used to: select a sample of GA or a polymeric precursor thereof for further use; select (e.g., as suitable for sale or for administration (e.g., injection) to a human) a sample of GA or a polymeric precursor thereof; classify, accept, release, process into drug product a sample of GA or a polymeric precursor thereof; select a sample of GA or a polymeric precursor thereof for shipment, moving to a new location, formulating, labeling, packaging, selling, offering for sale, releasing into commerce; and/or select a sample of GA or a polymeric precursor thereof for use in a manufacturing process for GA.

The methods described herein can also include selecting to discard, withhold, reprocess through a previous manufacturing step, or discontinue use of, GA or a polymeric precursor of GA, for example, if portion of the GA or the polymeric precursor that is alpha helical does not meet a preselected relationship, is not within, is not equivalent to, and/or is not consistent with a value or range shown in Table 1.

Methods for Determining Secondary Structure

As noted above, the disclosure provides methods for measuring, assessing, determining the secondary structure (e.g., portion of alpha helical structure and or random coil structure in GA and/or a polymeric precursor of GA. Other methods not explicitly disclosed herein may also be used so long as they allow measurement of the portion of GA that is alpha helical or random coil, e.g., in 10 mM sodium phosphate (pH 7.0) at 5° C.

EXAMPLES

The invention is further described in the following examples, which do not limit the scope of the invention described in the claims.

Example 1

Secondary Structure Analysis of Reference Listed Drug

Copaxone® was analyzed by CD spectroscopy. The sample matrix was 10 mM sodium phosphate buffer (pH 7.0). The drug substance was present at 0.2 mg/mL. Detailed analysis of solution conditions had shown that the presence of mannitol at the level in the drug product had no effect on the measured CD spectra. Thus, drug substance and drug product could be used interchangeably.

Wavelength scans were made between 195 nm and 245 nm at 5° C. An estimate of the α-helical content was made using the two-state model using the spectra for poly-lysine in alpha-helical form and the spectra for poly-lysine in random coil form described in: "Computed Circular Dichroism Spectra for the Evaluation of Protein Conformation" (Greenfield and Fasman, *Biochemistry*, 8:4108-4116, 1969)) as reference spectra.

Secondary structural analysis of 28 lots of Copaxone® was carried out essentially as described above (10 mM sodium phosphate buffer (pH 7.0), 0.2 mg/mL drug substance at 5° C.). For the 28 lots analyzed, the minimum and maximum alpha-helical content were 56.6% and 61.9%, respectively.

Example 2

Secondary Structure Analysis of GA

Samples from three lots of GA were analyzed by CD spectroscopy to assess secondary structure. This analysis was carried out essentially as described above in Example 1. The alpha helical content in the three lots was: 62.7%, 58.9% and 55.7%. In each case, random coil conformation account for the remainder of the secondary structure.

Example 3

Impact of Variation in GA Synthesis on Secondary Structure

Various materials were prepared by varying the process for producing GA by altering the timing of NCA addition or the length of the polymerization step. The secondary structure of the resulting materials was assessed essentially as described above in Example 1. It was found that the alpha-helical content of these materials varied from 11% to 65% showing that changes in the GA manufacturing process can alter the secondary structure of the material produced.

Example 4

Data Analysis

As discussed above, a two-state model considering only the alpha helix and random coil conformations can be used for analyzing the CD spectra of GA. The following least square method can be used, as can other suitable approaches to deconvolution.

$$\theta_i = a^* \alpha_i + r^* \gamma_i$$

$$\epsilon_i = \theta_i - a^* \alpha_i - r^* \gamma_i$$

$$0 = \delta/\delta a \{\Sigma \epsilon_i^2\} = 2^* a^* \Sigma \alpha_i^2 - 2^* \Sigma \alpha_i \theta_i + 2^* r^* \Sigma \alpha_i \gamma_i$$

$$0 = \delta/\delta r \{\Sigma \epsilon_i^2\} = 2^* r^* \Sigma \gamma_i^2 - 2^* \Sigma \gamma_i \theta_i + 2^* a^* \Sigma \alpha_i \gamma_i$$

$$a^* \Sigma \alpha_i^2 + r^* \Sigma \alpha_i \gamma_i = \Sigma \alpha_i \theta_i$$

$$r^* \Sigma \gamma_i^2 + a^* \Sigma \alpha_i \gamma_i = \Sigma \gamma_i \theta_i$$

$$a = \{\Sigma \alpha_i \theta_i^* \Sigma \gamma_i^2 - \Sigma \alpha_i \gamma_i^* \Sigma \gamma_i \theta_i\} / \{\Sigma \alpha_i^{2*} \Sigma \gamma_i^2 - [\Sigma \alpha_i \gamma_i]^2\}$$

$$r = \{\Sigma \gamma_i \theta_i^* \Sigma \alpha_i^2 - \Sigma \alpha_i \gamma_i^* \Sigma \alpha_i \theta_i\} / \{\Sigma \alpha_i^{2*} \Sigma \gamma_i^2 - [\Sigma \alpha_i \gamma_i]^2\}$$

$$a = \{C^* \Sigma \alpha_i \theta_i - A^* \Sigma \gamma_i \theta_i\}/D$$

$$r = \{B^* \Sigma \gamma_i \theta_i - A^* \Sigma \alpha_i \theta_i\}/D$$

Where $A = \Sigma \alpha_i \gamma_i$; $B = \Sigma \alpha_i^2$; $C = \Sigma \gamma_i^2$; $D = B^*C - A^2$ $\theta_i$—Measured ellipticity
$\alpha_i$—ellipticity corresponding to pure alpha conformation
$\gamma_i$—ellipticity corresponding to pure random coil conformation
i—the wavelength index
$\epsilon_i$—the random error contribution—for least square analysis
a and r are the respective mole fractions sought by the analysis The following basis set data (Table 2) can be used in the analysis. The data is from "Computed circular dichroism spectra for the evaluation of Protein conformation" (Greenfield and Fasman, *Biochemistry*, 8:4108-4116, 1969).

TABLE 2

| Wavelength | Alpha-helix | Random coil |
|---|---|---|
| 200 | 14.3 | −36.4 |
| 202 | 0 | −25.6 |
| 205 | −25 | −14.5 |
| 208 | −32.6 | −3.4 |
| 210 | −32.4 | −1.4 |
| 211 | −32.1 | 0 |
| 214 | −31 | 3.5 |

TABLE 2-continued

| Wavelength | Alpha-helix | Random coil |
|---|---|---|
| 215 | −31.4 | 4.1 |
| 217 | −33.1 | 4.6 |
| 220 | −35.3 | 4.4 |
| 222 | −35.7 | 3.9 |
| 225 | −32.4 | 2.7 |
| 230 | −21.9 | 0.8 |
| 234 | −11.4 | 0 |
| 238 | −4.3 | −0.14 |
| 240 | −3.3 | −0.15 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of manufacturing a glatiramer acetate drug product, the method comprising:
   (a) providing a batch of a composition comprising glatiramer acetate;
   (b) measuring one or both of alpha helical content of the glatiramer acetate and random coil content of the glatiramer acetate in the batch using a method that comprises obtaining and analyzing a circular dichroism spectrum of a sample of the batch using a model that assumes that all of the glatiramer acetate is either alpha helical conformation or random coil conformation;
   (c) determining whether or not i) the measured alpha helical content of glatiramer acetate in the batch is 53.8% to 65.0% under reference conditions, ii) the measured random coil content of glatiramer acetate in the batch is 46.2% to 35.0% under reference conditions, or iii) the measured alpha helical content of glatiramer acetate in the batch is 53.8% to 65.0% under reference conditions and the measured random coil content of glatiramer acetate in the batch is 46.2% to 35.0% under reference conditions, wherein the reference conditions are 5° C. in 10 mM sodium phosphate at pH 7.0; and
   (d) based on the determining step, manufacturing or not manufacturing a glatiramer acetate drug product using at least a portion of the batch.

2. The method of claim 1 wherein the step of providing a batch of a composition comprising glatiramer acetate comprises: polymerizing an N-carboxy anhydride of L-alanine, an N-carboxy anhydride of benzyl-protected L-glutamic acid, an N-carboxy anhydride of trifluoroacetic acid (TFA) protected L-lysine and an N-carboxy anhydride of L-tyrosine to generate a protected copolymer; and treating the protected copolymer to partially depolymerize the protected copolymer, deprotect benzyl protected groups and deprotect TFA-protected lysines.

3. The method of claim 1 wherein the step of manufacturing a glatiramer acetate drug product comprises adding mannitol to at least a portion of the batch.

4. The method of claim 1, wherein it is determined that: i) the measured alpha helical content of glatiramer acetate in the batch is 53.8% to 65.0% under reference conditions, ii) the measured random coil content of glatiramer acetate in the batch is 46.2% to 35.0% under reference conditions, or iii) the measured alpha helical content of glatiramer acetate in the batch is 53.8% to 65.0% under reference conditions and the measured random coil content of glatiramer acetate in the batch is 46.2% to 35.0% under reference conditions; and wherein a glatiramer acetate drug product is manufactured using at least a portion of the batch.

5. The method of claim 4, wherein the step of manufacturing a glatiramer acetate drug product comprises adding mannitol to at least a portion of the batch.

6. A method of preparing a pharmaceutical composition comprising glatiramer acetate, the method comprising:
   (a) providing a batch of a composition comprising a copolymer of tyrosine, lysine, alanine and glutamic acid;
   (b) measuring one or both of alpha helical content of the copolymer and random coil content of the copolymer in the batch using a method that comprises obtaining and analyzing a circular dichroism spectrum of a sample of the batch using a model that assumes that all of the copolymer is either alpha helical conformation or random coil conformation; (c) determining whether or not i) the measured alpha helical content of copolymer in the batch is 53.8% to 65.0% under reference conditions, ii) the measured random coil content of copolymer in the batch is 46.2% to 35.0% under reference conditions, or iii) the measured alpha helical content of copolymer in the batch is 53.8% to 65.0% under reference conditions and the measured random coil content of copolymer in the batch is 46.2% to 35.0% under reference conditions, wherein the reference conditions are 5° C. in 10 mM sodium phosphate at pH 7.0; and
   (d) based on the determining step, preparing or not preparing a pharmaceutical composition comprising glatiramer acetate using at least a portion of the batch, wherein the step of preparing a pharmaceutical composition comprises adding mannitol.

7. The method of claim 6 wherein the step of providing a batch of a composition comprising a copolymer of tyrosine, lysine, alanine and glutamic acid comprises: polymerizing an N-carboxy anhydride of L-alanine, an N-carboxy anhydride of benzyl-protected L-glutamic acid, an N-carboxy anhydride of trifluoroacetic acid (TFA) protected L-lysine and an N-carboxy anhydride of L-tyrosine to generate a protected copolymer; and treating the protected copolymer to partially depolymerize the protected copolymer, deprotect benzyl protected groups and deprotect TFA-protected lysines.

8. The method of claim 6 wherein the copolymer is glatiramer acetate drug substance.

9. The method of claim 6, wherein it is determined that: i) the measured alpha helical content of copolymer in the batch is 53.8% to 65.0% under reference conditions, ii) the measured random coil content of copolymer in the batch is 46.2% to 35.0% under reference conditions, or iii) the measured alpha helical content of copolymer in the batch is 53.8% to 65.0% under reference conditions; and wherein a pharmaceutical composition comprising glatiramer acetate is prepared using at least a portion of the batch.

* * * * *